US006555381B2

(12) United States Patent
Baugh et al.

(10) Patent No.: US 6,555,381 B2
(45) Date of Patent: Apr. 29, 2003

(54) METHOD FOR DETERMINING A CONTACT ACTIVATOR FOR PLATELET ACTIVATION

(75) Inventors: Robert F. Baugh, Parker, CO (US); Carole G. Lane, Greenwood Village, CO (US); Adrian C. Wilson, Denver, CO (US)

(73) Assignee: Medtronic, Inc., Minneapolis, MN (US)

( * ) Notice: Subject to any disclaimer, the term of this patent is extended or adjusted under 35 U.S.C. 154(b) by 83 days.

(21) Appl. No.: 09/810,740

(22) Filed: Mar. 16, 2001

(65) Prior Publication Data

US 2001/0018215 A1 Aug. 30, 2001

Related U.S. Application Data

(60) Division of application No. 09/225,051, filed on Jan. 4, 1999, now Pat. No. 6,221,672, which is a continuation-in-part of application No. 08/640,277, filed on Apr. 30, 1996, now abandoned.

(51) Int. Cl.$^7$ .......................... G01N 33/86; C12Q 1/56
(52) U.S. Cl. ..................... 436/69; 436/10; 422/73; 435/4; 435/13
(58) Field of Search .................. 436/69, 10; 422/73; 435/4, 13

(56) References Cited

U.S. PATENT DOCUMENTS

| | | | |
|---|---|---|---|
| 3,985,618 A | 10/1976 | Innerfield | 195/103.5 R |
| 4,000,972 A | 1/1977 | Baun et al. | 23/230 |
| 4,443,408 A | 4/1984 | Mintz | 422/73 |
| 4,533,519 A | 8/1985 | Baugh | 422/73 |
| 4,551,308 A | 11/1985 | Mintz | 422/58 |
| 4,599,219 A | 7/1986 | Cooper et al. | 422/61 |
| 4,671,939 A | 6/1987 | Mintz | 422/58 |
| 4,720,787 A | 1/1988 | Lipscomb | 364/416 |
| 4,782,026 A | 11/1988 | Baugh et al. | 436/69 |
| 4,871,677 A | 10/1989 | Baugh et al. | 436/69 |
| 5,174,961 A | 12/1992 | Smith | 422/73 |
| 5,207,988 A | 5/1993 | Lucas | 422/73 |
| 5,266,462 A | 11/1993 | Hemker et al. | 435/13 |
| 5,314,826 A | 5/1994 | Baugh | 436/69 |
| 5,441,892 A | 8/1995 | Baugh | 436/69 |
| 5,472,852 A | 12/1995 | Smirnov et al. | 453/13 |
| 5,505,721 A | 4/1996 | Leach et al. | 604/403 |
| 5,525,477 A | 6/1996 | Hassouna | 435/13 |
| 5,525,478 A | 6/1996 | Matschiner | 435/13 |
| 5,563,041 A | 10/1996 | Reers | 435/13 |
| 5,925,319 A | 7/1999 | Baugh et al. | 422/73 |
| 5,951,951 A | 9/1999 | Lane et al. | 422/73 |
| 5,972,712 A | 10/1999 | Baugh et al. | 436/69 |
| 6,010,911 A | 1/2000 | Baugh et al. | 436/69 |
| 6,221,672 B1 * | 4/2001 | Baugh et al. | 422/73 |
| 6,300,135 B1 * | 10/2001 | Isogawa et al. | 252/408.1 |

FOREIGN PATENT DOCUMENTS

| DE | 0 661 383 A | 12/1994 |
|---|---|---|
| US | WO 93/25578 A | 12/1993 |

* cited by examiner

*Primary Examiner*—Jill Warden
*Assistant Examiner*—Monique T Cole
(74) *Attorney, Agent, or Firm*—Steven C. Peterson; Sarah S. O'Rourke; Hogan & Hartson LLP

(57) ABSTRACT

A method of determining a contact activator for platelet activation and/or clotting activation is provided, comprising placing a predetermined amount of an anticoagulant in each cell of a multicell test cartridge, placing a predetermined amount of a platelet inactivating agent in each cell, and placing a measured amount of contact activator in each cell, the amount of contact activator in each cell differing from the amount in each other cell. An aliquot of a blood sample is added to each cell, and the blood sample aliquot, clotting reagent and platelet inactivating agent are mixed. Each cell sample is allowed to clot, and the clotting time for each cell is measured. The relative clotting times are used to determine the platelet activation and/or clotting activation effect of the clotting activator.

19 Claims, 4 Drawing Sheets

METHOD FOR DETERMINING A CONTACT ACTIVATOR FOR PLATELET ACTIVATION

CROSS-REFERENCE TO OTHER APPLICATIONS

This patent application is a divisional application of U.S. patent application Ser. No. 09/225,051, filed Jan. 4, 1999, and entitled "Method for Determining Platelet Inhibitor Response," now issued as U.S. Pat. No. 6,221,672, which is a continuation-in-part of U.S. patent application Ser. No. 08/640,277, filed Apr. 30, 1996 now abandoned, and entitled "Method For Determining Platelet Inhibitor Response", now abandoned, all of which are specifically incorporated herein by reference.

BACKGROUND OF THE INVENTION

1. Field of the Invention

The present invention relates to measuring and determining the effectiveness of antiplatelet reagents or platelet function inhibitors in the coagulation of blood.

More specifically, the present invention relates to a method of determining the effectiveness of antiplatelet reagents or platelet inhibitors on the mechanical activation of platelets.

2. Description of the Prior Art

Blood coagulation is a complex chemical and physical reaction which occurs when blood comes into contact with an activating agent, such as an activating surface or an activating reagent. In accordance with one simplified conceptual view, the whole blood coagulation process can be generally viewed as three activities: agglutination of platelets, blood clotting, and fibrous tissue formation. In vivo, platelets flow through the blood vessels in an inactivated state because the blood vessel lining, the endothelium, prevents activation of platelets. When a blood vessel is damaged, however, the endothelium loses its inert character and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting proceeds.

If the chemical balance of the blood is suitable, thrombin is then produced which causes conversion of fibrinogen to fibrin, which forms the major portion of the clot mass. During clotting, additional platelets are activated and trapped in the forming clot, contributing to clot formation. As clotting proceeds, polymerization and cross-linking of fibrin serves as the permanent clot. Thus, platelet activation plays a very important function in blood coagulation.

A number of different medical apparatuses and testing methods exist for measuring and determining coagulation and coagulation-related activities of blood. These apparatuses and methods provide valuable medical information to an attending physician. For example, the information assists a physician in prescribing medication, predicting post-operative bleeding and prescribing various therapies. Some of the more successful techniques of evaluating blood clotting and coagulation are the plunger techniques illustrated by U.S. Pat. No. 4,599,219 to Cooper et al., U.S. Pat. No. 4,752,449 to Jackson et al., and U.S. Pat. No. 5,174,961 to Smith, all of which are assigned to the assignee of the present invention, and all of which are incorporated herein by reference.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends on the actuator by the force of gravity, resisted by a property of the fluid in the reaction chamber, such as its viscosity. When the property of the sample changes in a predetermined manner as a result of the onset or occurrence of a coagulation-related activity, the descent rate of the plunger assembly therethrough is changed. Upon a sufficient change in the descent rate, the coagulation-related activity is detected and indicated by the apparatus.

Certain discoveries have recently been made which contribute to a better understanding of the role of platelets in an activated clotting time (ACT) test. Such discoveries suggest that the activation of the platelets has a significant and previously unappreciated effect on ACT test results. It has long been suspected that platelet activation contributes to total blood coagulation times, but there has been no technique available for confirming and quantifying the impact of platelet activation on ACT. It has been discovered that the initial contact and interaction of the blood sample with the activating reagent has an impact on the platelet activation, which may make the ACT test results variable and operator dependent. Without understanding and controlling the effect of platelet activation on the ACT there is a probability of inconsistent and inaccurate clinical test results. The degree and extent of the impact may depend on operator technique, but the impact and the extent of the impact has been unappreciated and unquantified. No previously known ACT test has intentionally taken into account the effect of platelet activation on the test results.

In developing and testing the improved high sensitivity coagulation detection apparatus employing the plunger technique, described in U.S. Pat. No. 5,174,961, (referred to hereinafter as the "second generation ACT apparatus") identical blood samples were tested on both the second generation ACT apparatus and the assignee's earlier apparatus, illustrated by that described in U.S. Pat. No. 4,752,449 (referred to hereinafter as the "first generation ACT apparatus"). When results obtained by the second generation ACT apparatus were compared with the results obtained from the first generation ACT apparatus, it was discovered that with identical blood samples and identical test cartridges, the second generation ACT apparatus produced consistently longer coagulation times than the first generation ACT apparatus. It was also noted that a still earlier and different version of the assignee's apparatus (referred to hereinafter as the "HMS apparatus") produced coagulation times similar to those of the second generation ACT apparatus. The principal difference noted between the first and second generation of ACT apparatus, that also differentiated the first generation ACT apparatus from the HMS apparatus, was that both the second generation ACT apparatus and the HMS apparatus reciprocate the plunger at a relatively high rate, while the first generation ACT apparatus reciprocates the plunger at a relatively slower rate, during initial mixing of the sample with the activation reagent. The faster reciprocation rate of the second generation ACT apparatus is desirable during testing because the faster rate results in increased sensitivity for detection of clot formation during the test.

While the reasons for the discoveries described herein may not be completely understood at this time, it is believed that upon initial contact of the blood with the activating reagent, the platelets are very susceptible to the amount and type of agitation they encounter. In accordance with this belief, platelets are visualized as coming into contact with activating particles and being activated at the surface of the particle. Slowly lowering the flag-plunger assembly leads to the generation of low shear forces within the blood sample bringing the platelets into better contact with the activating particles thus allowing the platelets to adhere to the particles, achieving full activation. Under these conditions the platelets in the blood sample rapidly activate in which they expose platelet factor 3 activity and possibly release platelet factor 4 activity. Under the conditions of the assay, activation of both of these components will shorten the blood clotting time. However, if the shear rate in the blood sample is changed to higher shear forces by increasing the fall rate of the flag-plunger, the more violent agitation may strip the platelets from the surface of the activating reagent particles before the platelets are fully activated, thus prolonging or adding the previously unappreciated variability of some measure of uncontrolled platelet activation to the amount of time required to achieve clotting in an ACT test.

Although previous apparatuses using the plunger sensing technique have proven generally satisfactory, the need for certain enhancements has been identified. Specifically, while these techniques can measure and detect coagulation and coagulation-related activities in a sample of blood, none are designed to conveniently measure and determine the effectiveness of antiplatelet reagents or platelet function inhibitors on the mechanical activation of platelets.

A need therefore exists for a method of determining the effectiveness of therapeutic levels of platelet function inhibitors in a variety of circumstances. Until this invention, no such devices or methods existed.

SUMMARY OF THE INVENTION

It is the principal object of the present invention to provide an improved method for measuring and determining the effectiveness of antiplatelet reagents or platelet inhibitors on the coagulation of blood.

A further object of the present invention is to provide a method of determining the effectiveness of antiplatelet reagents or platelet function inhibitors on the mechanical activation of platelets.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, the present invention is directed to a method of determining a dose response for a platelet inhibitor. The method includes the steps of placing a predetermined amount of heparin in each cell of a multicell test cartridge, placing an optimized amount of a mechanical platelet and/or clotting activator in each cell, and placing a measured amount of platelet inhibitor in each cell, the amount of inhibitor in each cell differing from the amount in each other cell. An aliquot of a blood sample is added to each cell, and the blood sample aliquot, platelet and/or clotting activator and platelet inhibitor are mixed. Each cell sample is allowed to clot, and the clotting time for each cell is measured. The relative clotting times are used to calculate and determine the platelet inhibition effect of the platelet inhibitor.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings.

DESCRIPTION OF THE PREFERRED EMBODIMENT

Figure 1:
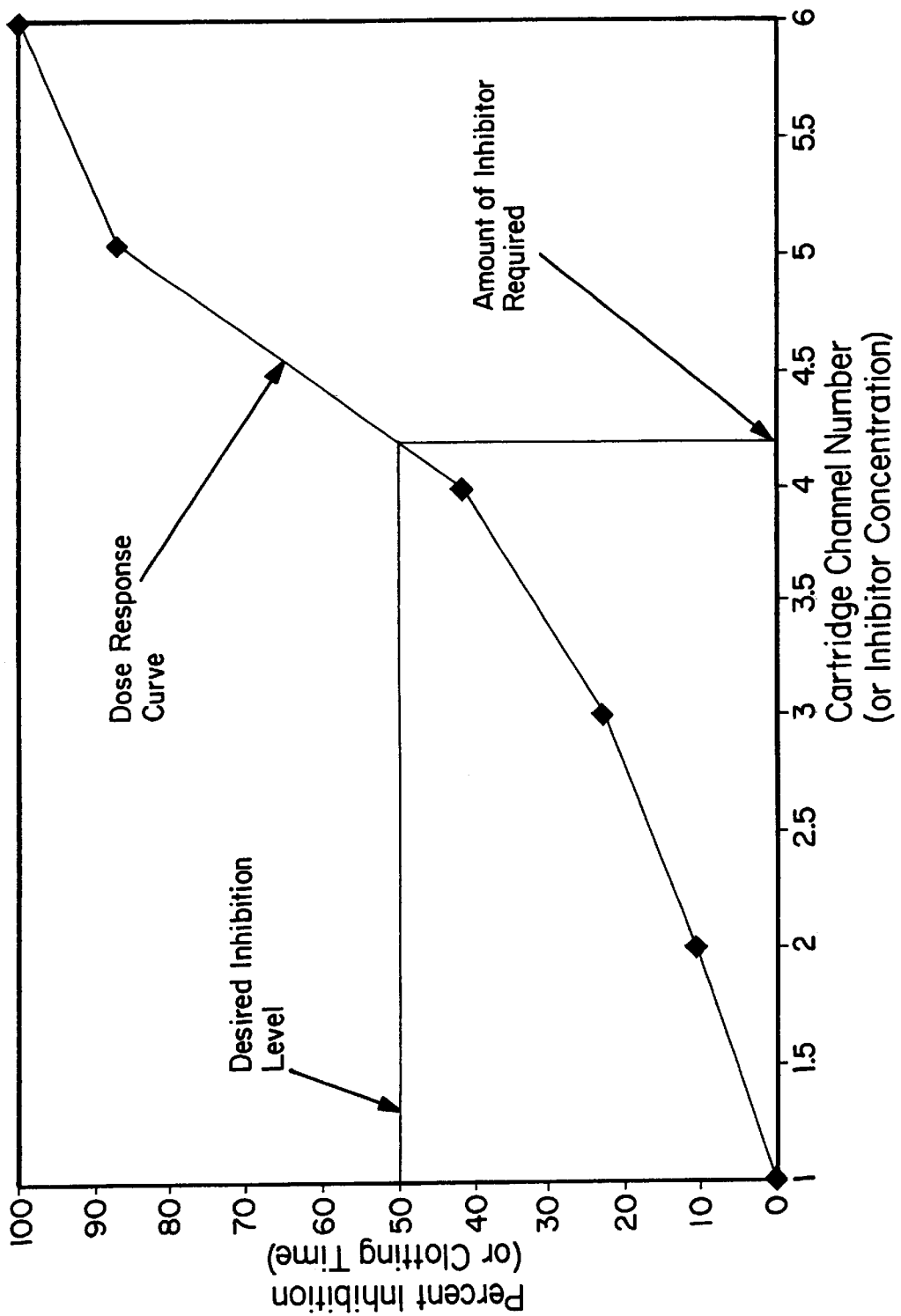
FIG. 1 is a hypothetical graph of Percent Inhibition vs. Inhibitor Concentration.

In accordance with the present invention, it has been discovered that the ability of platelet inhibitors or antiplatelet drugs to effect coagulation of blood can be readily assessed. To this end, by using different concentrations of a platelet inhibitor in a plurality of test cells, and using an optimized amount of a mechanical contact activator of platelets and/or clotting, the ability of an inhibitor in a selected dose to prevent the mechanical activation of platelets can be assessed.

To practice the method for measuring and determining the effectiveness of antiplatelet reagents or platelet function inhibitors on the mechanical activation of platelets of the present invention, each of test cells 66 (shown in FIGS. 3 and 4 and discussed in further detail below) includes a novel reagent composition. This novel reagent composition (shown in FIG. 4 as reagent composition 80 in reaction chamber 94) may be either a liquid or a solid powder, and includes two components: an anticoagulant agent, and a platelet inhibitor agent.

The anticoagulant agent of the reagent composition 80 accentuates the rate-limiting step in coagulation. The anticoagulant agent may be any substance having anticoagulant activity and which is not affected by factors derived (released) from activated platelet. A wide variety of suitable anticoagulant compounds are known and are readily available in the art including, for example, but not limited to, heparin, argatroban and other synthetic or natural compounds which are specific inhibitors of thrombin and/or clotting factor Xa. Preferably, the anticoagulant agent is a substrate-derived competitive thrombin inhibitor, such as synthetic peptides, arginine derivatives, benzamidine derivatives, and lysine derivatives. In a particularly preferred embodiment, heparin is the anticoagulant agent of choice since it is necessary to inhibit reactions which occur later in the coagulation process, such as activation of factors X, II (prothrombin) and I (fibrinogen), i.e., reactions in the common pathway or in a later stage in the intrinsic pathway. By inhibiting these later clotting factors, heparin (which together with antithrombin III accelerates the inactivation of factor X and thrombin) helps to accentuate the contribution of platelets to clotting, which is the rate-limiting step in blood coagulation, i.e., the actual clotting times in the ACT test depend on how rapidly the platelets are able to activate clotting. Accordingly, heparin must be either present in the blood sample or included in the reagent composition 80 to inhibit non-platelet-related reactions which tend to obscure the rate-limiting activation step.

The concentration of the anticoagulant agent in reagent composition 80 required to achieve sufficient test sensitivity will depend upon the anticoagulant activity of the particular agent and the level of sensitivity desired. With the presently preferred anticoagulant agent, heparin, the reagent concentration is preferably between about 1 to 4 units/ml, and more preferably between about 2 to about 4 units/ml.

The final component of the novel reagent composition 80 of the present invention is a platelet inhibiting agent which serves as the chemical platelet inhibitor to facilitate evaluation of the function of platelets in the blood sample to be tested. If the platelets are inactive or not functioning normally, the platelet inhibiting agent will have a lessened or no effect on the clotting time. Platelet inhibiting agents are well known and readily available in the art. Two classes of platelet inhibitors exist; the first class comprises compounds that act on platelet membrane sites, broadly known as IIa/IIb inhibitors such as, but not limited to, Abciximab, which is the Fab fragment of the chimeric human-murine monoclonal antibody 7E3 and sold under the trademark ReoPro™, or 4-[4-[4-(aminoiminomethyl)phenyl]-1-piperazinyl]-1-piperidineacetic acid, hydrochloride trihydrate sold under the trademark GR144053™. The second class comprises compounds that are metabolic inhibitors such as, but not limited to, acetylsalicylic acid or aspirin.

Figure 4:
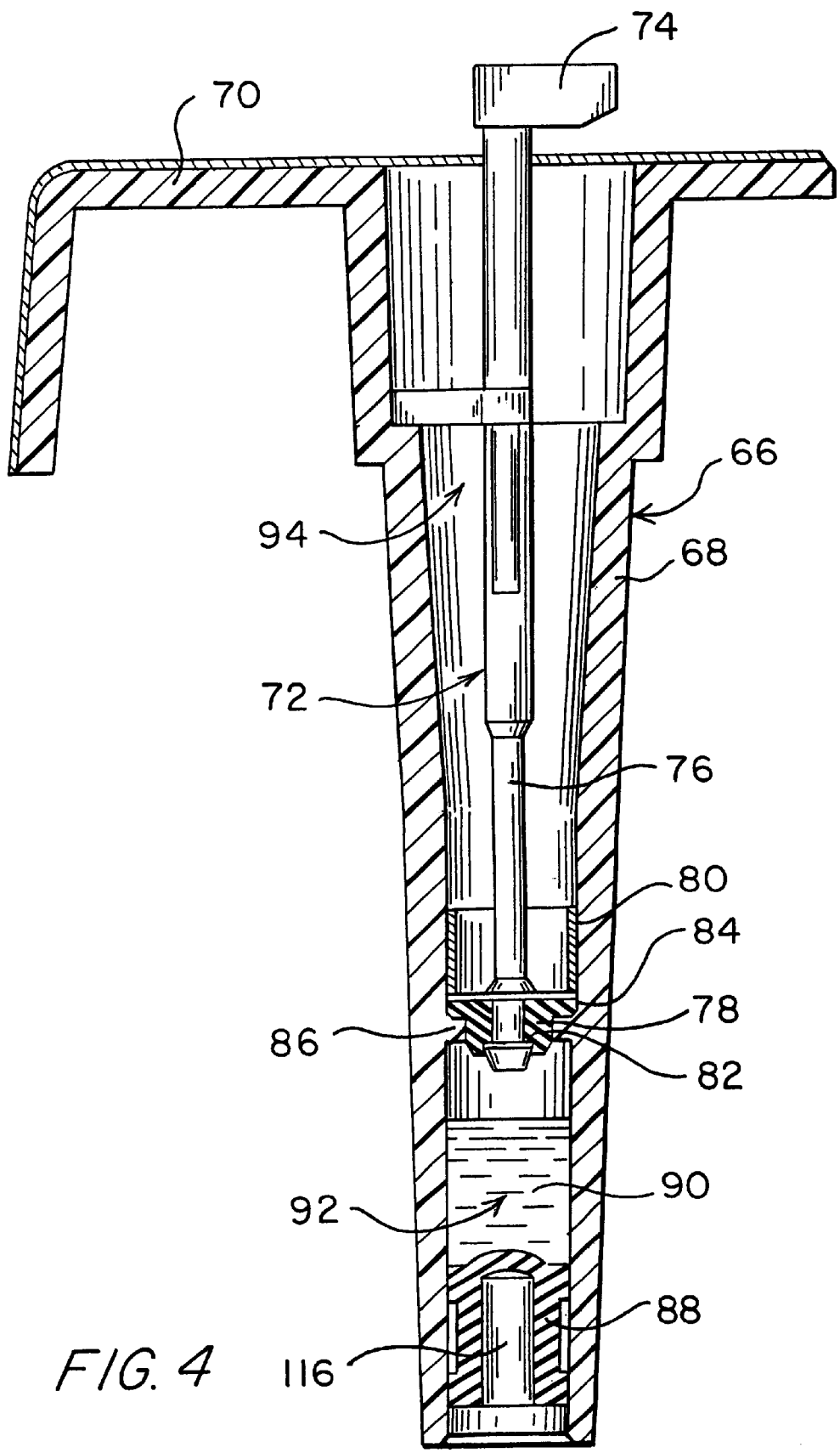
FIG. 4 is an enlarged vertical sectional view through one of the test cells of the plunger sensor cartridge, taken in the plane of line 4—4 shown in FIG. 3.

The specific concentrations of the platelet inhibiting agent in reagent composition 80 of the present invention (i.e., reagent composition 80 in reaction chamber 94 of the test cell 66, shown in FIG. 4) will depend, in part, upon the specific antiplatelet compound to be tested, but regardless varying amounts will be used in each test cells 66 so that selected doses can be assessed for the ability to prevent mechanical activation of platelets.

As discussed previously, reagent composition 80 of the present invention may be either a liquid or a solid powder, although a solid powder form (commonly referred to as a "dry fill") is preferred. To prepare reagent composition 80 as a solid or dry fill, predetermined amounts of the two components (anticoagulant agent, and platelet inactivating agent) are combined and mixed with a saline (NaCl) solution preferably containing a protein, such as bovine serum albumin, to stabilize the platelet inactivating agent. The mixture may be diluted, if necessary, with additional saline solution to achieve the desired platelet inactivating agent concentrations. A predetermined amount of each solution of reagent composition 80 is placed in the reaction chambers 94 of the test cells 66 (shown in FIGS. 2, 3 and 4) and allowed to evaporate, leaving a solid or dry fill residue of reagent composition 80.

The method and apparatus of the present invention also includes a contact activator in the reagent chamber (shown in FIG. 4 as reagent chamber 92) of each test cell 66. The contact activator (discussed below and shown in FIG. 4 as contact activator 90) includes an activator (commonly referred to as a surface activator), such as kaolin, to activate platelets and blood Factors XII and/or XI. However, as will be appreciated by those of skill in the art, other contact activators which function in a similar manner to kaolin may be used for the practice of the invention, such as diatomaceous earth, powdered glass, silica, or any other particle having a negatively charged surface. Activators may be chosen by simply performing the method of the present invention with differing activators and comparing the magnitude of clotting time. Kaolin is preferable however, since it is an activator of both coagulation and platelets. If desired, one could also use a contact activator of platelets in combination with a contact activator of coagulation. The contact activator 90 may be present in either a solid or liquid form, although the presently preferred reagent is in a liquid form. To prepare a liquid contact activator 90, the activator component may be dissolved in an appropriate buffered solution, a variety of which are known to those skilled in the art, including HEPES (hydroxyethyl-piperazine ethanesulfonic acid) buffer. A bacteriostatic agent such as sodium azide may also be included in clotting reagent 90. In a particularly preferred embodiment, contact activator 90 comprises kaolin, HEPES buffer, calcium chloride (to achieve a linear clotting time response to heparin), and sodium azide as the bacteriostatic agent. Kaolin in the amount of 2% to 15% and preferably 4% to 12% may be used. One illustrative composition is HEPES buffer, 50 mM calcium chloride, 0.02% sodium azide as a bacterio-static agent, and 4% kaolin, at pH 7.4.

In order to provide a series of differing clotting times, at least two of the test cells comprise different amounts of the platelet inactivating agent. In the exemplified embodiment shown in FIG. 3, the first two cells 66A and 66B (which represent the "baseline" or non-activated clotting time) contain no platelet inhibiting agent. Each successive cell 66C, 66D, 66E, and 66F includes increasing amounts of platelet inhibiting agent. Although the concentrations and proportions may vary depending upon the particular reagent components (as discussed above), the following table provides an illustration of suitable amounts of the presently preferred components in reagent composition 80, prior to dilution with the blood sample:

TABLE 1

Amounts of Components in Reagent Composition 80
(Test Cartridge 64)

| Reagent | Cell 66A | Cell 66B | Cell 66C | Cell 66D | Cell 66E | Cell 66F |
|---|---|---|---|---|---|---|
| Platelet Inhibitor | 0.0 ng | 0.0 ng | X | aX | bX | cX |
| Heparin | 3.0 U | 3.0 U | 3.0 U | 3.0 U | 3.0 U | 3.0 U |

The actual concentrations cannot be given until a specific antiplatelet compound is tested in the system. X represents a low concentration of the compound with which inhibition (or an increase in the clotting time) is just noticeable. Factors a, b, and c represent multiple increases in the amount of the compound X added to the cells. Concentration cX is preferably an excess of the compound, in order to give maximal inhibition of platelet activation. Increasing the amount of the antiplatelet drug above this concentration will not further increase the clotting time.

To determine the platelet inhibition in accordance with one embodiment of the present invention, a predetermined volume of blood to be analyzed is introduced into the reaction chamber 94 of each test cell 66A–66F, thereby dissolving reagent composition 80. The contact activator 90 in each reagent chamber 92 is then introduced into the corresponding reaction chamber of each test cell 66A–66F, at a low shear force mode. At the termination of the "mix cycle," the agitator is switched to a drop rate in the high shear force mode and the clotting time is determined. The clot ratio is then calculated based on the clotting time for each test cell. When all six cells have clotted, the test is terminated and a relative clotting time is computed wherein the clotting times of the cells containing no platelet inhibitor are used as the reference clotting time. The simplest calculation is to consider this zero percent inhibition, and the cell with the maximum amount or excess of the inhibitor is considered as 100% inhibition. The clotting times from the intermediate cells are then compared to determine the dose response.

Figure 2:
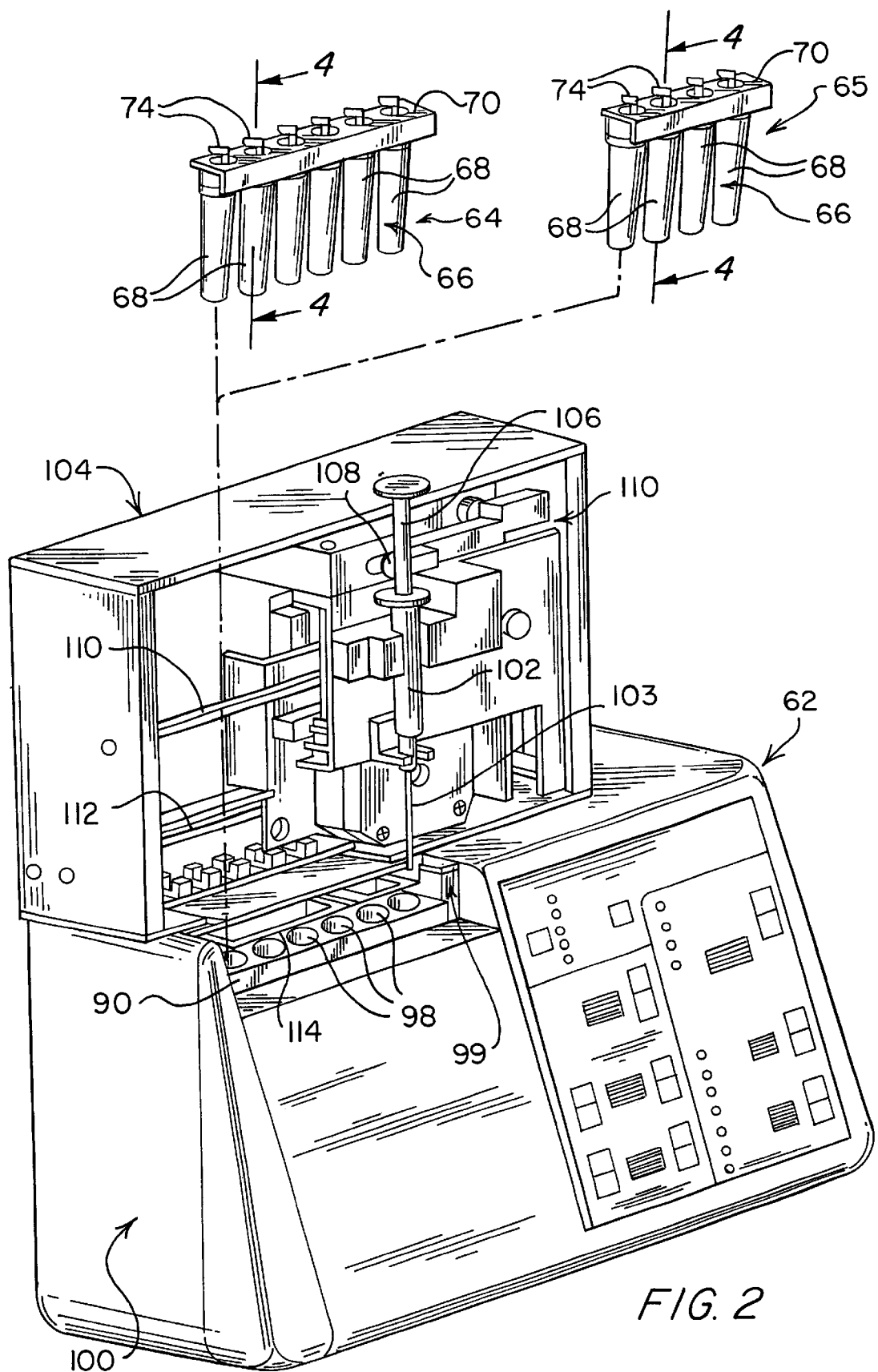
FIG. 2 is a perspective view of a 6-channel plunger sensor cartridge, a 4-channel plunger sensor cartridge, and a high sensitivity coagulation detection apparatus with which the cartridges are used on selectively alternate basis, all of which comprises an apparatus for measuring and detecting coagulation and coagulation-related factors in fluids, in accordance with the present invention.
Figure 3:
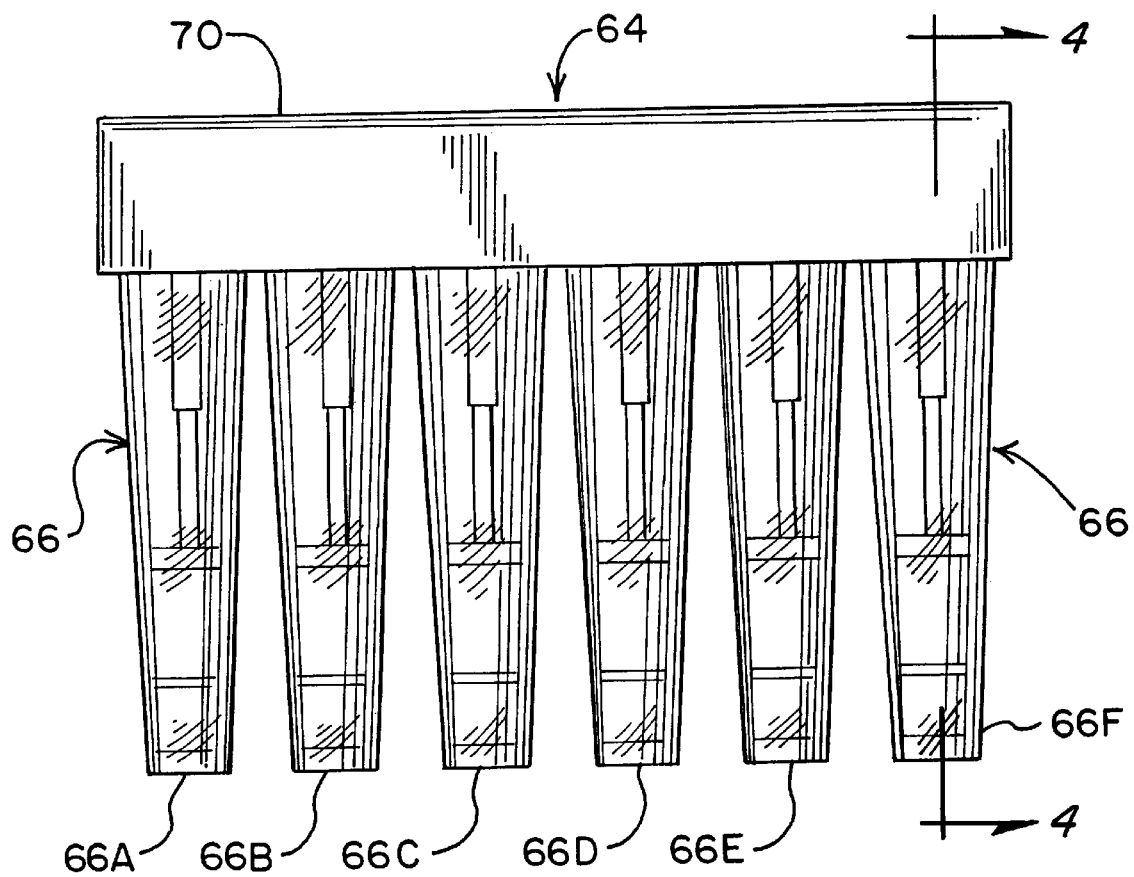
FIG. 3 is a front elevational view of the 6-channel plunger sensor cartridge shown in FIG. 2.

Referring now to FIGS. 2, 3 and 4, the presently preferred embodiment of an apparatus 62 and a plunger sensor cartridge 64 may be used together in order to evaluate the effectiveness of antiplatelet reagents or platelet inhibitors on the mechanical activation of platelets. The apparatus 62 and an alternate cartridge 65 can also be used to perform a platelet inhibition test using these unique reagents. In general, the ACT test and other heparin-protamine titration tests which may be performed using the apparatus 62 and the cartridges 64, 65 have previously been described in the assignee's aforementioned patents and applications, including U.S. Pat. No. 4,599,219 and U.S. Ser. No. 08/640,275, now issued as U.S. Pat. No. 5,925,319, the disclosures of which are incorporated herein by reference. Accordingly, many of the details of functionality will be generalized herein with the understanding that the assignee's prior patents and applications disclose many of these details to a greater extent. It is anticipated that similar results and effects as those obtained from using the assignee's plunger sensor technique will also be obtainable by practicing the present invention using other well known methods and devices.

In general, the cartridges 64, 65 as shown in FIGS. 2 and 3 include a plurality of test cells 66 (shown in FIG. 4), each of which is formed generally as a downward extending truncated tube-like member 68. Each of the tube-like members 68 is connected to an upper shelf portion 70. A plunger assembly 72 (shown in FIG. 4) extends downward from an upper open end of each test cell 66 into the tube-like member 68. Each plunger assembly 72 includes at least one and preferably a pair of flags 74 at the upper end located at a position above the shelf portion 70. The plunger assembly 72 also includes a shaft 76 which extends from the flags 74 downward to a lower end upon which a disk member 78 is attached. The disk member 78 is formed of resilient material and includes a center, generally cylindrical main body portion 82 and an annular flange 84 located above and extending outward from the main body portion 82. The annular flange 84 includes slots or openings (not shown) formed therein at outer circumferential locations.

As shown in FIG. 4, prior to using the plunger sensor cartridge 64 or 65 in the apparatus 62, the disk member 78 is positioned with its main body portion 82 located in and sealed against an opening formed by a partition 86 extending inwardly from the tube-like member 68. The partition 86 is located between the upper and lower open ends of the tube-like member 68. A resilient flexible plug 88 is positioned in the interior of the tube-like member at its lower open end. The plug 88 seals against the inner side walls of the tube-like member 68 and confines a quantity of contact activator 90 (discussed above) in a reagent chamber 92 between the partition 86 and the plug 88. The clotting reagent 90 may be a liquid or a solid powder. A reaction chamber 94 is generally defined by that portion of the open tube-like member 68 above the partition 86. A predetermined amount of a reagent composition 80, the contents of which have been described in detail above, is provided in the reaction chamber 94 as either a liquid or a solid powder.

The plunger sensor cartridge 64 or 65 is inserted into a receiving block (not shown) in the apparatus 62 to conduct the ACT test. Each of the test cells 66 extends into a receptacle 98 of the receiving block. Each receptacle 98 has a configuration adapted to receive a test cell 66, while the shelf portion 70 of the cartridge 64 or 65 sits on top of the receiving block.

The apparatus 62 is generally formed of subassemblies. A dispensing subassembly 104 of the apparatus 62 automatically supplies a sample of blood to each test cell 66 of the cartridge 64 or 65. The reagent composition 80 is dissolved in the blood sample when the blood sample is introduced into the reaction chamber 94. A plunger lifting assembly 99 of the apparatus 62 controls the lifting movement of the plunger assembly 72, and a reagent drive subassembly 100 of the apparatus 62 moves the plug 88 to force the clotting reagent 90 into the reaction chamber 94, thereby mixing the clotting reagent 90 with the reagent composition 80. An optical sensing system (not shown) senses the physical descent of the plunger assembly 72 through the blood sample and reagent mixture in the reaction chamber 94 in order to detect coagulation condition.

The sample of blood is supplied to the reaction chamber 94 from a syringe 102 having a blunt needle 103 attached thereto. The syringe 102 is manually attached to the dispensing subassembly 104 of the apparatus 62. The body of the syringe 102 contains blood, preferably fresh drawn from the patient, upon which the ACT test is to be performed. Of course, prior to attachment of the syringe 102 to the dispensing subassembly 104, all air or other voids in the blood within the syringe 102 and the blunt needle 103 is removed in the conventional manner. A plunger 106 located within the body of the syringe 102 is engaged with a drive wheel 108. Rotation of the drive wheel 108 forces the syringe plunger 106 downward and expels a predetermined amount of blood from the lower end of the blunt needle 103. The extent to which the syringe plunger 106 is moved downward determines the quantity of blood expelled from the needle.

The dispensing subassembly 104 includes a movement frame 110 which is moved laterally in the horizontal direction along guide rods 112. The degree of lateral movement is controlled by the microprocessor (not shown) of the apparatus 62 in accordance with programmed information, thereby locating the blunt needle 103 directly above the open upward ends of each test cell 66 of the cartridge 64 or 65. After attaining the proper lateral location, the movement frame 110 moves the syringe 102 vertically downward to insert the lower end of the blunt needle 103 into each of the test cells 66. The desired amount of fluid sample is automatically dispensed into the test cell 66. Thereafter, the blunt needle 103 is withdrawn from the test cell 66 by the movement frame 110, and the next lateral position over a test cell 66 is assumed. The sequence again repeats itself, thereby injecting into each test cell 66 of the plunger sensor cartridge 64 or 65 that predetermined amount of blood sample needed for conducting the ACT-type test.

A portion of the plunger lifting subassembly 99 is shown in FIG. 2, and includes at least one and preferably a plurality of lift wires 114. The lift wires 114 are positioned in a lowermost location, and in that position a horizontal segment of the lift wires 114 fits underneath the flags 74 of the plunger assembly 72. Upward movement of the lift wires 114 lifts each of the plunger assemblies 72 upward, thereby removing the disk member 78 from its sealed location in the opening 84 of the partition 86. A fluid communication passageway through the opening 84 between the reagent chamber 92 and the reaction chamber 94 is thereby established. The reagent drive subassembly 100 includes a plurality of plug driver shafts 116 (shown in FIG. 4). Thereafter, or simultaneously with the upward movement of the plunger assembly 72, the plug driver shafts 116 of the reagent drive subassembly 100 move upward, forcing each plug 88 upward collapsing the reagent chamber 92 and forcing its contents 90 into the reaction chamber 94.

At the commencement of the ACT-type test, a sample of blood upon which the test is to be performed is introduced into the reaction chamber 94. The lift wires 114 of the subassembly 99 lift the plunger assembly 72 to withdraw the disk member 78 from its seated engagement with the opening in the partition 86. The plug 88 is pushed upward against the partition 86 by the plug driver shafts 116 of the subassembly 100. The contact activator 90 from the reagent chamber 92 is forced through the opening into the reaction chamber 94. The contact activator 90 is mixed with the blood and reagent mixture in the reaction chamber 94, by reciprocating the plunger assembly 72 at a low shear force for a predetermined period of time of about 8 to 60 seconds. The lift wires 114 of the subassembly 99 continue to lift the plunger assembly 72, which descends by the force of gravity through the pool of fluid in the reaction chamber 94. At the termination of this first period of time, the plunger assembly is switched to a drop rate in a high shear force mode. This optimizes the ability to detect clot formation. Clotting time is then measured in each test cell. As the plunger assembly 72 descends through the fluid it is resisted by a property of the fluid in the reaction chamber 94, such as the viscosity, which changes as a result of the onset or occurrence of a coagulation-related activity, e.g., platelet activation and aggregation followed by coagulation resulting in fibrin formation. The descent rate of the plunger assembly 72 therethrough is changed, which indicates the occurrence of a coagulation-related activity.

When all six cells have clotted, the test is terminated and a relative clotting time is computed wherein the clotting times of the cells containing no platelet inhibitor are used as the reference clotting time. The simplest calculation is to consider this zero percent inhibition, and the cell with the maximum amount or excess of the inhibitor is considered as 100% inhibition. The clotting times from the intermediate cells are then compared to determine the dose response.

The purpose of the foregoing test is three-fold: 1) to determine an individual's basic response to the platelet inhibitor, 2) to monitor the presence of the platelet inhibitor, and 3) to determine the quantitative concentration of the inhibitor.

To illustrate the use of the present invention, a dose response cartridge test is performed on a patient using compound X as a specific platelet inhibitor. A titration curve is plotted which is used to compute a dosage of the drug which will be given to the patient. The test apparatus computes this dosage based on the clotting times and the program which relates to this specific drug. After giving the patient the drug, a two channel activated clotting time assay is performed. This measures whether or not the target clotting time has been achieved and is a measure of the effectiveness of the drug.

If a specific concentration of the drug is desired, this may be determined by using the previous dose response curve obtained to compute the concentration of the inhibitor. Alternatively, if a chemical or antibody exists which will neutralize the platelet inhibitor, the concentration of the platelet inhibitor can be determined using a titration cartridge containing varying amounts of the neutralizing chemical.

FIG. 1 illustrates a process in which the desired degree of platelet inhibition is a 50% inhibition. The Y-axis is computed from the clotting times obtained using the above-described dose response assay cartridge. The clinician enters the 50% inhibition figure into the apparatus and the apparatus computes the information given in FIG. 1. Using FIG. 1, the horizontal line labeled "Desired Inhibition Level" represents 50% inhibition. This line intersects the "Dose Response Curve." A vertical line is dropped from this point of intersection to the X-axis where the intersection of the line with the X-axis provides the concentration of inhibitor required to achieve 50% inhibition of the platelets. FIG. 1 is labeled in terms of cell numbers, but could also be labeled with concentrations of the inhibitor, from zero in cell 1 to the maximum (100% inhibition) in cell 6.

In monitoring the effectiveness of the drug, the above dose response curve can be used after running a two channel assay cartridge, taking the clotting time (the Y-axis could also be given in terms of the clotting times rather than a percentage of inhibition). This is used to convert the clotting time to a concentration of the inhibitor using the same type of calculation as above.

A third method for determining the amount of platelet drug present uses a titration assay. This requires that a chemical or antibody capable of neutralizing the inhibitor be available. In a titration cartridge, each channel of the assay cartridge contains increasing amounts of the neutralizing agent. The channel where the shortest clotting time is obtained is the concentration of neutralizing agent where all of the platelet inhibitor has been neutralized. Knowing the stoichiometry between the neutralizing agent and the platelet inhibitor, the concentration of the platelet inhibitor present in the sample can be computed.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The embodiments of the invention in which an exclusive property or privilege is claimed are defined as follows:

1. A method for determining a contact activator for platelet activation and/or clotting activation using a coagulation detection apparatus, said apparatus comprising a first, a second and a third test cell, each of said cells comprising an anticoagulant and a platelet inactivating agent wherein said first cell further comprises a first contact activator, said second cell further comprises a second contact activator and said third cell does not contain a contact activator, said method comprising:
   a) dividing the sample of blood into first, second and third partial samples;
   b) dispensing the first partial sample into the first test cell to form a first test mixture;
   c) performing a first activated clotting time test on the first test mixture to obtain a first clotting time;
   d) repeating the aforementioned steps of dispensing and performing an activated clotting time test on each of said second and third partial samples to obtain a second and third clotting time; and
   e) comparing the activated clotting times of the first, second, and third partial samples to determine whether the contact activator functions to mechanically activate platelets and/or clotting.

2. The method of claim 1, wherein said first and second contact activators comprise particles having negatively charged surfaces.

3. The method of claim 1, wherein the comparing step further comprises preparing a titration curve by plotting the activated clotting times of the first, second, and third partial samples.

4. The method of claim 1, wherein said anticoagulant is heparin.

5. The method of claim 4, wherein the amount of heparin in each cell is between about 1 unit and about 4 units per milliliter of blood sample.

6. The method of claim 1, wherein said platelet inactivating agent is selected from the group consisting of Abciximab, 4-[4-[4-(aminoiminomethyl)phenyl]-1-piperazinyl]-1-piperidineacetic acid, hydrochloride trihydrate, and acetylsalicylic acid.

7. The method of claim 2, wherein one of said contact activators is kaolin.

8. The method of claim 2, wherein one of said contact activators is diatomaceous earth.

9. The method of claim 2, wherein one of said contact activators is powdered glass.

10. The method of claim 2, wherein one of said contact activators is silica.

11. A method of determining a dose response for a contact activator for platelet activation and/or clotting activation, said method comprising:
   a) placing a predetermined amount of anticoagulant in each cell of a multicell test cartridge;
   b) placing predetermined amount of a platelet inactivating agent in each said cell;
   c) placing a measured amount of said contact activator in each said cell, the amount of said contact activator in each cell differing from the amount in each other cell;
   d) adding an aliquot of a blood sample to each said cell, mixing said blood sample aliquot, contact activator and platelet inactivating agent;
   e) clotting each cell sample and measuring the clotting time for each said cell; and
   f) computing the relative clotting times to determine the platelet activation and/or clotting activation effect of the contact activator.

12. The method of claim 11, wherein said anticoagulant is heparin.

13. The method of claim 12, wherein the amount of heparin in each cell is between about 1 unit and about 4 units per milliliter of blood sample.

14. The method of claim 11, wherein the contact activator comprises particles having negatively charged particles.

15. The method of claim 14, wherein said contact activator is kaolin.

16. The method of claim 14, wherein said contact activator is diatomaceous earth.

17. The method of claim 14, wherein said contact activator is powdered glass.

18. The method of claim 14, wherein said contact activator is silica.

19. The method of claim 11, wherein said platelet inactivating agent is selected from the group consisting of Abciximab, 4-[4-[4-(aminoiminomethyl)phenyl]-1-piperazinyl]-1-piperidineacetic acid, hydrochloride trihydrate, and acetylsalicylic acid.

* * * * *